United States Patent

Bormann et al.

[11] 4,057,560
[45] Nov. 8, 1977

[54] 1,2,2,a,3,4,5 HEXAHYDROBENZ[c,d]INDOL-1-YL-2 GUANIDINES

[75] Inventors: Gerhard Bormann, Munchenstein; Franz Troxler, Bottmingen, both of Switzerland

[73] Assignee: Sandoz Ltd., Basel, Switzerland

[21] Appl. No.: 487,194

[22] Filed: July 10, 1974

[30] Foreign Application Priority Data

July 16, 1973 Switzerland .................. 10327/73
July 16, 1973 Switzerland .................. 10328/73

[51] Int. Cl.[2] .......................................... C07D 209/90
[52] U.S. Cl. .................. 260/326.86; 260/326.84; 424/274
[58] Field of Search ............ 260/313.1, 326.5 B, 260/326.5 S, 326.86, 326.84

[56] References Cited

U.S. PATENT DOCUMENTS

| 3,030,378 | 4/1962 | Mull .................. 260/326.86 |
| 3,304,306 | 2/1967 | Werner et al. ........... 260/326.86 |
| 3,674,801 | 7/1972 | Bormann et al. ......... 260/313.1 |

FOREIGN PATENT DOCUMENTS

| 517,730 | 2/1972 | Switzerland ............ 260/326.5 F |
| 517,732 | 4/1972 | Switzerland ............ 260/326.5 F |

OTHER PUBLICATIONS

Burger, "Medicinal Chemistry," 3rd Ed., p. 71, Interscience (1970).
Bormann et al.,—Chem. Abst., vol. 74, (1971) p. 125427d.

*Primary Examiner*—Donald G. Daus
*Assistant Examiner*—D. B. Springer
*Attorney, Agent, or Firm*—Gerald D. Sharkin; Robert S. Honor; Thomas O. McGovern

[57] ABSTRACT

The present invention concerns novel compounds of formula I,

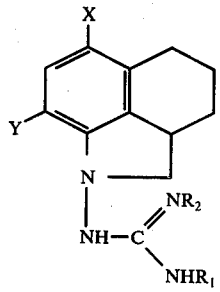

wherein
$R_1$ is hydroxy, or

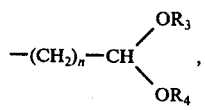

wherein
$n$ is an integer from 1 to 5, and
$R_3$ and $R_4$ are independently alkyl of 1 to 4 carbon atoms, or
$R_3$ and $R_4$ together form an alkylene chain of 2 or 3 carbon atoms,
$R_2$ is hydrogen, alkyl of 1 to 4 carbon atoms, phenylalkyl of 7 to 9 carbon atoms, or phenylalkyl of 7 to 9 carbon atoms mono- or disubstituted on the phenyl radical by halogen, alkyl of 1 to 4 carbon atoms or alkoxy of 1 to 4 carbon atoms, and
either
X is hydrogen, and
Y is methyl,
or
X is methylthio or dialkylamino, wherein the alkyl chains are independently of 1 to 4 carbon atoms, and
Y is hydrogen,
or
X is chlorine or bromine, and
Y is chlorine,
or, when $R_1$ is the above acetal group, X also signifies hydrogen, chlorine, bromine or methyl, and Y signifies hydrogen,
useful as salidiuretics.

28 Claims, No Drawings

1,2,2a,3,4,5 HEXAHYDROBENZ[c,d]INDOL-1-YL-2-GUANIDINES

The present invention relates to new heterocyclic compounds.

In accordance with the invention there are provided new compounds of formula I,

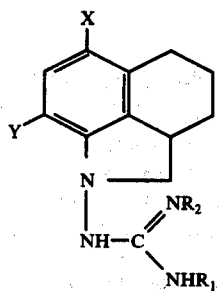

wherein
R₁ is hydroxy, or

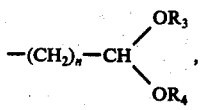

wherein
n is an integer from 1 to 5, and
R₃ and R₄ are independently alkyl of 1 to 4 carbon atoms, or
R₃ and R₄ together form an alkylene chain of 2 or 3 carbon atoms, R₂ is hydrogen, alkyl of 1 to 4 carbon atoms, phenylalkyl of 7 to 9 carbon atoms, or phenylalkyl of 7 to 9 carbon atoms mono- or disubstituted on the phenyl radical by halogen, alkyl of 1 to 4 carbon atoms or alkoxy of 1 to 4 carbon atoms, and
either
X is hydrogen, and
Y is methyl,
or
X is methylthio or dialkylamino, wherein the alkyl chains are independently of 1 to 4 carbon atoms, and
Y is hydrogen,
or
X is chlorine or bromine, and
Y is chlorine,
or, when R₁ is the above acetal group, X also signifies hydrogen, chlorine, bromine or methyl, and Y signifies hydrogen.

The symbol n especially signifies 1 or 2.

When R₃ and R₄ are alkyl, these groups especially contain 1 or 2 carbon atoms; when R₃ and R₄ together form an alkylene chain, this especially contains two carbon atoms.

When R₂ is alkyl, this especially contains 1 or 2 carbon atoms. When R₂ is phenylalkyl, the alkyl chain thereof especially contains 1 or 2 carbon atoms, and any alkyl or alkoxy substituents of the phenyl radical especially contain 1 or 2 carbon atoms.

When X is dialkylamino, the alkyl chains thereof especially contain 1 or 2 carbon atoms.

Halogen especially signifies chlorine or bromine, preferably chlorine.

Further, in accordance with the invention a compound of formula I may be obtained by a process comprising reacting a compound of formula II,

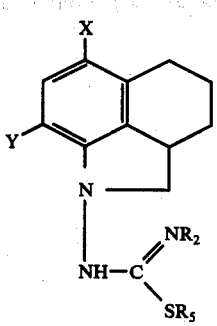

wherein
X, Y and R₂ are as defined above, and
R₅ is alkyl of 1 to 4 carbon atoms,
with a compound of formula III, $$H_2N-R_1 \qquad \qquad III$$

wherein R₁ is as defined above.

R₅ especially signifies methyl.

The production of compounds of formula I in accordance with the invention may be effected in a manner analogous to the known methods for the production of guanidine compounds.

The reaction of compounds of formula II with compounds of formula III in accordance with the invention is conveniently effected in the presence of a mineral acid e.g. bound in the form of an amine acid addition salt. The reaction is preferably effected in the presence of at least one equivalent of a mineral acid calculated on the compound of formula II. It is preferred to effect the reaction with at least some compound of formula II and compound of formula III in unprotonated form.

The reaction may, for example, be effected by reacting an acid addition salt of a compound of formula II, e.g. the hydrochloride, hydrobromide, hydriodide or sulphate, with an excess of a compound of formula III. The preferred molar ratio of a salt of a compound of formula II to a compound of formula III is about 1:2 to 1:6. The reaction may be effected at an elevated temperature; when R₁ is hydroxyl the reaction temperature preferably is between 65° and 100° C, when R₁ is an acetal group the reaction temperature preferably is about 120° C. The reaction may be effected in an inert organic solvent; when R₁ is hydroxy the reaction is preferably effected in an inert polar solvent, e.g. a lower alkanol such as ethanol, isopropanol, an amide of an organic carboxylic acid such as dimethyl formamide, an open chain or cyclic ether such as dioxane, or a mixture of the same with water. When R₁ is an acetal group, an excess of the compound of formula III used is preferably employed as solvent.

The guanidine compounds of formula I, produced in accordance with the process described above, may be isolated in the usual manner and may be purified in accordance with known methods. When R₁ is an acetal group and it is desired to isolate the compound in acid addition salt form, it must be taken into account that the acetal group is unstable to acids and, therefore, mild conditions must be used and an excess of acid must be avoided.

The compounds of formula II, required as starting materials, are in general known and may be produced in a manner analogous to the process described in U.S. Pat. No. 3,674,801, from corresponding compounds of formula IV,

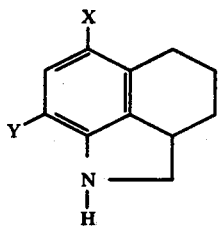

IV wherein X and Y are as defined above, as starting materials.

Of the compounds of formula IV, the compounds of formula IVa,

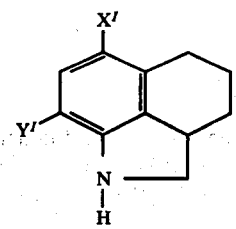

IVa wherein either
X′ is dialkylamino, wherein the alkyl chains contain 1 to 4 carbon atoms, and
Y′ is hydrogen,
or
X′ is bromine, and
Y′ is chlorine,
are new.

The compounds of formula IVa are obtained by deacetylation of the corresponding 1-acetyl compounds.

Compounds of formula V,

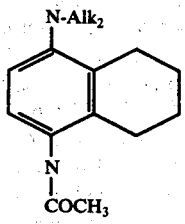

V wherein Alk is alkyl of 1 to 4 carbon atoms, may, for example, be obtained by nitrating 1-acetyl-1,2,2a,3,4,5-hexahydrobenz[c,d]indole, reducing the resulting 6-nitro compound to the corresponding 6-amino compound and alkylating this with alkyl iodide.

1-acetyl-6-bromo-8-chloro-1,2,2a,3,4,5-hexahydrobenz[c,d,]indole may, for example, be obtained by chlorinating 1-acetyl-6-bromo-1,2,2a,3,4,5-hexahydrobenz[c,d,]indole, e.g. with chlorine gas, in the presence of iron powder.

The compounds of formula III are known.

Free base forms of the compounds of formula I may be converted into acid addition salt forms in conventional manner and vice versa. Suitable inorganic acids include hydrochloric acid. Suitable organic acids include maleic acid.

Insofar as the production of the starting materials is not described, these are known or may be produced in accordance with known processes, or in a manner analogous to the processes described herein or to known processes.

In the following non-limitative Examples all temperature are indicated in degrees Centigrade and are uncorrected.

EXAMPLE 1

1-(1,2,2a,3,4,5-hexahydro-6-methylthiobenz-[c,d]indol-1-yl)-2-hydroxyguanidine 5.85 g of 1-(1,2,2a,3,4,5-hexahydro-6-methylthiobenz[c,d]indol-1-yl)-2-methylisothiourea hydrochloride and 4.9 g of hydroxylamine hydrochloride are suspended in 115 cc of ethanol, and after the addition of 3 g of potassium ethylate, heating to the boil is effected for 1½ hours. After cooling, the potassium chloride and excess hydroxylamine hydrochloride are removed by suction and the filtrate is evaporated to dryness. The evaporation residue is dissolved in ethanol, the solution is filtered until clear and concentrated. Ether is added to the clear solution, whereby the hydrochloride form of the title compound crystallizes and after recrystallization from ethanol/ether has an M.P of 172°-174°.

The following compounds are obtained in a manner analogous to that described in Example 1:

1-(6,8-dichloro-1,2,2a,3,4,5-hexahydrobenz[c,d]indol-1-yl)-2-hydroxyguanidine
(M.P. of the hydrochloride form 210°-211° from methanol/ether)
using 1-(6,8-dichloro-1,2,2a,3,4,5-hexahydrobenz[c,d,]indol-1-yl)-2-methylisothiourea hydrochloride as starting material;

1-(1,2,2a,3,4,5-hexahydro-8-methylbenz[c,d]indol-1-yl)-2-hydroxyguanidine
(M.P. of the hydrochloride form 176°-177° from ethanol/ether)
using 1-(1,2,2a,3,4,5-hexahydro-8-methylbenz[c,d]indol-1-yl)-2-methylisothiourea hydrochloride (M.P. 212°-214° from ethanol/ether) as starting material;

1-(6,8-dichloro-1,2,2a,3,4,5-hexahydrobenz[c,d]indol-1-yl)-2-hydroxy-3-methylguanidine
(M.P. of the hydrogen maleate form 124°-126° from methanol/ether)
using 1-(6,8-dichloro-1,2,2a,3,4,5-hexahydrobenz[c,d,]indol-1-yl)-2,3-dimethylisothiourea hydrochloride (M.P. 212°-214° from methanol/ether) as starting materials;

3-p-chlorobenzyl-1-(6,8-dichloro-1,2,2a,3,4,5-hexahydrobenz[c,d]indol-1-yl)-2-hydroxyguanidine
(M.P. 152°-153° from methanol/petroleum ether)
using 3-p-chlorobenzyl-1-(6,8dichloro-1,2,2a,3,4,5-hexahydrobenz[c,d]indol-1-yl)-2-methylisothiourea hydrochloride (M.P. 189°-191° from ethanol/ether) as starting material;

1-(6-bromo-8-chloro-1,2,2a,3,4,5-hexahydrobenz[c,d]-indol-1-yl)-2-hydroxyguanidine
(M.P. of the hydrochloride form 206°-207° from ethanol/ether)

using 1-(6-bromo-8-chloro-1,2,2a,3,4,5-hexahydrobenz[c,d]indol-1-yl)-2-methylisothiourea hydrochloride (M.P. 160°-162° from methanol/ether) as starting material;

1-(6-dimethylamino-1,2,2a,3,4,5-hexahydrobenz[c,d]indol-1-yl)-2-hydroxyguanidine
using 1-(6-dimethylamino-1,2,2a,3,4,5-hexahydrobenz[c,d]indol-1-yl)-2-methylisothiourea hydrochloride as starting material;

EXAMPLE 2

2-(2,2-diethoxyethyl)-1-(1,2,2a,3,4,5-hexahydro-8-methylbenz[c,d]indol-1-yl)guanidine 7.5 g of 1-(1,2,2a,3,4,5-hexahydro-8-methylbenz[c,d]indol-1-yl)-2-methylisothiourea hydrochloride and 10.2 g of aminoacetaldehyde diethyl acetal are heated to a bath temperature of 120° for 1½ hours. The excess aminoacetaldehyde diethyl acetal is removed by evaporation in a vacuum and the evaporation residue is extracted between ethyl acetate and 1 N caustic soda solution. The ethyl acetate phase which has been dried over magnesium sulphate is evaporated to dryness. The title compound crystallizes from ether/petroleum ether (M.P. 93°-95°).

The following compounds may be produced in a manner analogous to that described in Example 2:

1-(6-bromo-1,2,2a,3,4,5-hexahydrobenz[c,d]indol-1-yl)-2-(2,2-diethoxyethyl)guanidine
(M.P. 151°-153° from ethyl acetate)
using 1-(6-bromo-1,2,2a,3,4,5-hexahydrobenz[c,d]indol-1-yl)-2-methylisothiourea hydriodide (M.P. 187°-189° from methanol/ether) as starting material;

2-(2,2-diethoxyethyl)-1-(1,2,2a,3,4,5-hexahydrobenz[c,d]indol-1-yl)guanidine
(M.P. 98°-99° from ether/petroleum ether)
using 1-(1,2,2a,3,4,5-hexahydrobenz[c,d]indol-1-yl)-2-methylisothiourea hydriodide as starting material;

2-(2,2-diethoxyethyl)-1-(1,2,2a,3,4,5-hexahydro-6-methylthiobenz[c,d]indol-1-yl)guanidine
(M.P. of the acetate form 175°-177° from ethanol/ethyl acetate)
using 1-(1,2,2a,3,4,5-hexahydro-6-methylthiobenz[c,d]indol-1-yl)-2-methylisothiourea hydrochloride as starting material;

2-(2,2-diethoxyethyl)-1-(6,8-dichloro-1,2,2a,3,4,5-hexahydrobenz[c,d]indol-1-yl)-3-methylguanidine
(M.P. 156°-157° from methylene chloride/petroleum ether)
using 1-(6,8-dichloro-1,2,2a,3,4,5-hexahydrobenz[c,d]indol-1-yl)-2,3-dimethylisothiourea hydrochloride (M.P. 212°-214° from methanol/ether) as starting material;

1-(6-chloro-1,2,2a,3,4,5-hexahydrobenz[c,d]indol-1-yl)-2-(2,2-diethoxyethyl)guanidine
(M.P. 147°-149° from ethyl acetate)
using 1-(6-chloro-1,2,2a,3,4,5-hexahydrobenz[c,d]indol-1-yl)-2-methylisothiourea hydriodide as starting material;

2-(2,2-diethoxyethyl)-1-(6,8-dichloro-1,2,2a,3,4,5-hexahydrobenz[c,d]indol-1-yl)guanidine
(M.P. 167°-169° from ethyl acetate)
using 1-(6,8-dichloro-1,2,2a,3,4,5-hexahydrobenz[c,d]indol-1-yl)-2-methylisothiourea hydrochloride as starting material;

1-(6-bromo-8-chloro-1,2,2a,3,4,5-hexahydrobenz[c,d]indol-1-yl)-2-(2,2-diethoxyethyl)guanidine
(M.P. 166°-168° from ethyl acetate)
using 1-(6-bromo-8-chloro-1,2,2a,3,4,5-hexahydrobenz[c,d]indol-1-yl)-2-methylisothiourea hydrochloride (M.P. 160°-162° from methanol/ether) as starting material;

2-(3,3-diethoxypropyl)-1-(6,8-dichloro-1,2,2a,3,4,5-hexahydrobenz[c,d]indol-1-yl)guanidine
(M.P. 116°-118° from ether)
using 1-(6,8-dichloro-1,2,2a,3,4,5-hexahydrobenz[c,d]indol-1-yl)-2-methylisothiourea hydrochloride and 3-aminopropionaldehyde diethyl acetal as starting materials;

2-(4,4-diethoxybutyl)-1-(6,8-dichloro-1,2,2a,3,4,5-hexahydrobenz[c,d]indol-1-yl)guanidine
(M.P. 92°-93° from ether/petroleum ether)
using 1-(6,8-dichloro-1,2,2a,3,4,5-hexahydrobenz[c,d]indol-1-yl)-2-methylisothiourea hydrochloride and 4-aminobutyraldehyde diethyl acetal as starting materials;

-(6,8-dichloro-1,2,2a,3,4,5-hexahydrobenz[c,d]indol-1-yl)-2-[2-(1,3-dioxolan-2-yl)ethyl]guanidine
(M.P. 128°-130° from methylene chloride/petroleum ether)
using 1-(6,8-dichloro-1,2,2a,3,4,5-hexahydrobenz[c,d]indol-1-yl)-2-methylisothiourea hydrochloride and 2-(2-aminoethyl)-1,3-dioxolane as starting materials;

2-(2,2-diethoxyethyl)-1-(6-dimethylamino-1,2,2a,3,4,5-hexahydrobenz[c,d]indol-1-yl)guanidine
using 1-(6-dimethylamino-1,2,2a,3,4,5-hexahydrobenz[c,d]indol-1-yl)-2-methylisothiourea hydrochloride as starting material;

In analogous manner to that described in Example 2 there is obtained,
1-(6,8-dichloro-1,2,2a,3,4,5-hexahydrobenz[c,d]indol-1-yl)-2-(1,3-dioxolan-2-ylmethyl)guanidine, M.P. 181°-182° from methylene chloride/petroleum ether.

In analogous manner to that described in Example 1, there are obtained the following compounds of formula I, wherein X and Y are Cl and $R_1$ is OH and

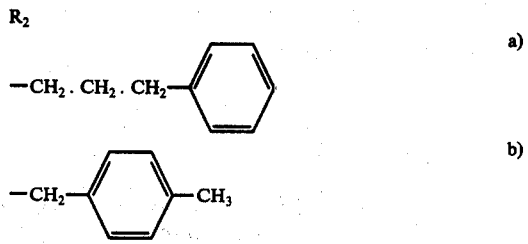

-continued c)

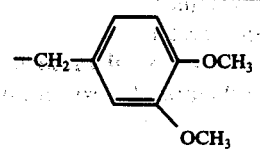

In analogous manner to that described in Example 2, there is obtained the compound of formula I, wherein X and Y are Cl, $R_2$ is H and $R_1$ is

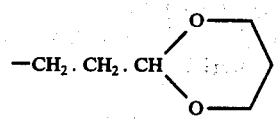

The compounds of formula I are useful as salidiuretic agents, e.g. for the treatment of oedema as indicated in standard animal tests, for example, in rats on p.o. administration of from about 1 to about 10 mg/kg animal body weight of the compounds in accordance with the principles of E. Flückiger et al., Schweiz med. W'schr., 93, 1232–1237 (1967).

For this use the dosage will, of course, vary depending on the compound employed, mode of administration and treatment desired. However, in general, satisfactory results are obtained when administered at a daily dosage of from about 0.1 mg to about 10 mg per kg animal body weight, conveniently given in divided doses 2 to 4 times a day or in sustained release form. For the larger mammals, the total daily dosage is in the range from about 5 to about 50 mg. and dosage forms suitable for oral administration comprise from about 1 mg to about 20 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

Suitable acids for acid addition salt formation include inorganic acids such as hydrogen iodide, hydrogen chloride or sulphuric acid and organic acids such as naphthalene-1,5-disulphonic acid, fumaric acid and maleic acid.

We claim:
1. A compound of formula I,

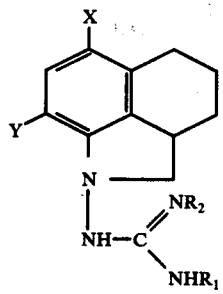

wherein
$R_1$ is hydroxy, or

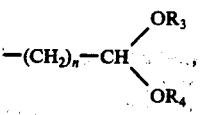

wherein
$n$ is an integer from 1 to 5, and
$R_3$ and $R_4$ are independently alkyl of 1 to 4 carbon atoms, or
$R_3$ and $R_4$ together form an alkylene chain of 2 or 3 carbon atoms,
$R_2$ is hydrogen, alkyl of 1 to 4 carbon atoms, phenylalkyl of 7 to 9 carbon atoms, or phenylalkyl of 7 to 9 carbon atoms mono- or disubstituted on the phenyl radical by halogen, alkyl of 1 to 4 carbon atoms or alkoxy of 1 to 4 carbon atoms, and
either
X is hydrogen, and
Y is methyl,
or
X is methylthio or dialkylamino, wherein the alkyl chains are independently of 1 to 4 carbon atoms, and
Y is hydrogen,
or
X is chlorine or bromine, and
Y is chlorine,
or, when $R_1$ is

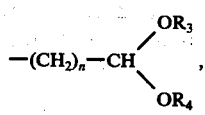

X also signifies hydrogen, chlorine, bromine or methyl, and Y signifies hydrogen
or a pharmaceutically acceptable acid addition salt thereof.

2. A compound of claim 1, wherein $R_1$ is hydroxy.
3. A compound of claim 2, wherein $R_2$ is hydrogen, alkyl or phenylalkyl of 7 to 9 carbon atoms substituted by halogen.
4. A compound of claim 1, wherein $R_2$ is hydrogen or alkyl.
5. A compound of claim 1 wherein X is methylthio and Y is hydrogen, X and Y are both chlorine and X is hydrogen and Y is methyl, $R_1$ is hydrogen and $R_2$ is hydroxy.
6. The compound of claim 1 which is 1-(6,8-dichloro-1,2,2a,3,4,5-hexahydrobenz[c,d]indol-1-yl)-2-hydroxyguanidine.
7. The compound of claim 1 which is 1-(1,2,2a,3,4,5-hexahydro-8-methylbenz[c,d]indol-1-yl)-2-hydroxyguanidine.
8. The compound of claim 1 which is 1-(6,8-dichloro-1,2,2a,3,4,5-hexahydrobenz[c,d]indol-1-yl)-2-hydroxy-3-methylguanidine.
9. The compound of claim 1 which is 3-p-chlorobenzyl-1-(6,8-dichloro-1,2,2a,3,4,5-hexahydrobenz[c,d]indol-1-yl)-2-hydroxyguanidine.
10. The compound of claim 1 which is 1-(6-bromo-8-chloro-1,2,2a,3,4,5-hexahydrobenz[c,d]indol-1-yl)-2-hydroxyguanidine.
11. A compound of claim 1 of the formula

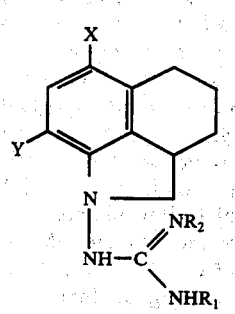

wherein
R$_1$ is hydroxy, or

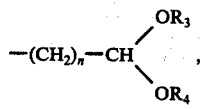

wherein
n is an integer from 1 to 5, and
R$_3$ and R$_4$ are independently alkyl of 1 to 4 carbon atoms, or
R$_3$ and R$_4$ together form an alkylene chain of 2 or 3 carbon atoms,
R$_2$ is hydrogen, alkyl of 1 to 4 carbon atoms, phenylalkyl of 7 to 9 carbon atoms, or phenylalkyl of 7 to 9 carbon atoms mono- or disubstituted on the phenyl radical by halogen, alkyl of 1 to 4 carbon atoms or alkoxy of 1 to 4 carbon atoms, and
 i. X is hydrogen, and
    Y is methyl;
 ii. X is hydrogen, chlorine, bromine, methyl, methylthio or dialkylamino, wherein the alkyl chains are independently of 1 to 4 carbon atoms, and
    Y is hydrogen; or
 iii. X is chlorine or bromine, and
    Y is chlorine, provided that when R$_1$ is hydroxy, X is methylthio or dialkylamino and Y is hydrogen,
or a pharmaceutically acceptable acid addition salt thereof.

12. A compound of claim 11 of the formula

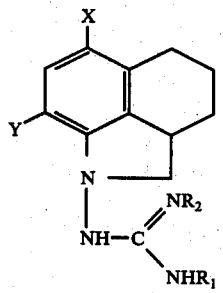

wherein
R$_1$ is hydroxy,
wherein
n is an integer from 1 to 5, and
R$_3$ and R$_4$ are independently alkyl of 1 to 4 carbon atoms, or
R$_3$ and R$_4$ together form an alkylene chain of 2 or 3 carbon atoms,
R$_2$ is hydrogen, alkyl of 1 to 4 carbon atoms, phenylalkyl of 7 to 9 carbon atoms, or phenylalkyl of 7 to 9 carbon atoms mono- or disubstituted on the phenyl radical by halogen, alkyl of 1 to 4 carbon atoms or alkoxy of 1 to 4 carbon atoms, and
X is methylthio or dialkylamino, wherein the alkyl chains are independently of 1 to 4 carbon atoms, and
Y is hydrogen,
or a pharmaceutically acceptable acid addition salt thereof.

13. The compound of claim 12 which is 1-(1,2,2a,3,4,5-hexahydro-6-methylthiobenz[c,d]indol1-yl)-2-hydroxyguanidine.

14. The compound of claim 12 which is 1-(6-dimethylamino-1,2,2a,3,4,5-hexahydrobenz[c,d]indol-1-yl)-2-hydroxyguanidine.

15. A compound of claim 11 of the formula

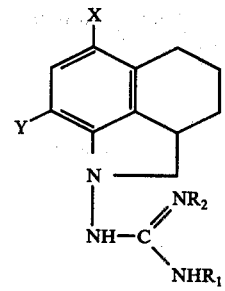

wherein
R$_1$ is

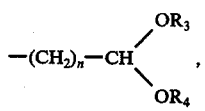

wherein
n is an integer from 1 to 5, and
R$_3$ and R$_4$ are independently alkyl of 1 to 4 carbon atoms, or
R$_3$ and R$_4$ together form an alkylene chain of 2 or 3 carbon atoms,
R$_2$ is hydrogen, alkyl of 1 to 4 carbon atoms, phenylaklyl of 7 to 9 carbon atoms, or phenylalkyl of 7 to 9 carbon atoms mono- or disubstituted on the phenyl radical by halogen, alkyl of 1 to 4 carbon atoms or alkoxy of 1 to 4 carbon atoms, and
 i. X is hydrogen, and
    Y is methyl;
 ii. X is hydrogen, chlorine, bromine, methyl, methylthio or dialkylamino, wherein the alkyl chains are independently of 1 to 4 carbon atoms, and
    Y is hydrogen; or
 iii. X is chlorine or bromine, and
    Y is chlorine,
or a pharmaceutically acceptable acid addition salt thereof.

16. A compound of claim 15, wherein X is chlorine, bromine, methyl or methylthio and Y is hydrogen; X is hydrogen and Y is methyl or X is chlorine and Y is chlorine, R$_2$ is hydrogen and R$_1$ is

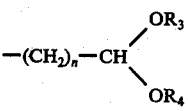

where n, R$_3$ and R$_4$ are as defined in claim 1.

17. The compound of claim 15 which is 2-(2,2-diethoxyethyl)-1-(1,2,2a,3,4,5-hexahydro-8-methylbenz[c,d]indol-1-yl)guanidine.

18. The compound of claim 15 which is 1-(6-bromo-1,2,2a,3,4,5-hexahydrobenz[c,d]indol-1-yl)-2-(2,2-diethoxyethyl)guanidine.

19. The compound of claim 15 which is 2-(2,2-diethoxyethyl)-1-(1,2,2a,3,4,5-hexahydrobenz[c,d]indol-1-yl)guanidine.

20. The compound of claim 15 which is 2-(2,2-diethoxyethyl)-1-(1,2,2a,3,4,5-hexahydro-6-methylthiobenz[c,d]indol-1-yl)guanidine.

21. The compound of claim 15 which is 2-(2,2-diethoxyethyl)-1-(6,8-dichloro-1,2,2a,3,4,5-hexahydrobenz[c,d]indol-1-yl)-3-methylguanidine.

22. The compound of claim 15 which is 1-(6-chloro-1,2,2a,3,4,5-hexahydrobenz[c,d]indol-1-yl)-2-(2,2-diethoxyethyl)guanidine.

23. The compound of claim 15 which is 2-(2,2-diethoxyethyl)-1-(6,8-dichloro-1,2,2a,3,4,5-hexahydrobenz[c,d]indol-1-yl)guanidine.

24. The compound of claim 15 which is 1-(6-bromo-8-chloro-1,2,2a,3,4,5-hexahydrobenz[c,d]indol-1-yl)-2-(2,2-diethoxyethyl)guanidine.

25. The compound of claim 15 which is 2-(3,3-diethoxypropyl)-1-(6,8-dichloro-1,2,2a,3,4,5-hexahydrobenz[c,d]indol-1-yl)guanidine.

26. The compound of claim 15 which is 2-(4,4-diethoxybutyl)-1-(6,8-dichloro-1,2,2a,3,4,5-hexahydrobenz[c,d]indol-1-yl)guanidine.

27. The compound of claim 15 which is 1-(6,8-dichloro-1,2,2a,3,4,5-hexahydrobenz[c,d]indol-1-yl)-2-[2-(1,3-dioxolan-2-yl)ethyl]guanidine.

28. The compound of claim 15 which is 2-(2,2-diethoxyethyl)-1-(6-dimethylamino-1,2,2a,3,4,5-hexahydrobenz[c,d]indol-1-yl)guanidine.

* * * * *